United States Patent [19]
Golbus

[11] Patent Number: 5,962,234
[45] Date of Patent: *Oct. 5, 1999

[54] USE OF ANTI-EMBRYONIC EPSILON HEMOGLOBIN ANTIBODIES TO IDENTIFY FETAL CELLS

[75] Inventor: Mitchell Golbus, Tiberon, Calif.

[73] Assignee: Applied Imaging Corporation, Santa Clara, Calif.

[*] Notice: This patent is subject to a terminal disclaimer.

[21] Appl. No.: 09/101,364

[22] PCT Filed: Oct. 20, 1997

[86] PCT No.: PCT/US97/19447

§ 371 Date: Sep. 25, 1998

§ 102(e) Date: Sep. 25, 1998

[87] PCT Pub. No.: WO98/18005

PCT Pub. Date: Apr. 30, 1998

[51] Int. Cl.[6] .................................................. G01N 33/53
[52] U.S. Cl. ........................... 435/7.1; 435/7.5; 435/7.72; 435/7.9; 435/7.92; 435/7.94; 435/40.5; 435/40.51; 436/518; 436/524; 436/527; 436/66; 530/385; 530/388.7; 530/389.6
[58] Field of Search ............................ 435/4, 6, 7.1, 7.5, 435/7.72, 7.9, 7.92, 7.94, 40.5, 40.51, 975; 436/510, 518, 524, 527, 66, 800; 530/380, 385, 388.2, 388.7, 389.6; 939/76, 77, 78

[56] References Cited

U.S. PATENT DOCUMENTS 5,731,156  3/1998  Golbus .

FOREIGN PATENT DOCUMENTS

WO 91/07660  5/1991  WIPO .
WO 94/17209  8/1994  WIPO .
WO 95/03431  2/1995  WIPO .

OTHER PUBLICATIONS

Zheng et al. "Flow Sorting of Fetal Erythroblasts Using Intracytoplasmic Anti–Fetal Haemoglobin: Preliminary Observations on Maternal Samples", *Prenatal Diagnosis*, vol. 15(1995), pp. 897–905.
Kutlar et al. "Quantities of Adult, Fetal and Embryonic Globin Chains in the Blood of Eighteen–to Twenty–Week–Old Human Fetuses", *Journal of Chromatography*, vol. 567, No. 2(Jul. 5, 1991), pp. 359–368. Abstract Only, complete reference unavailable at this time.
Pierce Catalog, 1992–1993, Rockford, IL, 800–8–Pierce, pp. D1–3 and D29–31. TP202.P43.
Saunder et al. "Enrichment of Fetal Cells From Maternal Blood for Genetic Analysis", *Abstracts of the American Society of Human Genetics*, A287, abstract No. 1672(1995).
Bianchi, et al., "Prenatal Diagnosis by analysis of fetal cells in material blood", *J. Pediatr.*, 127(6): 847–856 (1995).
Bianchi, et al., "Isolation of Fetal DNA from Nucleated Erythrocytes in Maternal Blood", *Proc. Natl. Acad. Sci. USA*, 87:3279–3283 (1990).
Bischoff, et al., "Fetal cells in maternal blood: more efficacious Fish analysis by using gamma globin mRNA to identify fetal cells after flow–sorting," *Abstracts of American Journal of Human Genetics*, 57(4 Suppl.):A33 #162 (1995).
Chueh and Globus. "The Search for Fetal Cells in the Maternal Circulation," *J. Perinat. Med.*, 19:411–420 (1991).
Chueh and Golbus, "Prenatal Diagnosis Using Fetal Cells from Maternal Circulation," *West. J. Med.*, 159(3):308–311 (1993).
Cheung, et al., "Prenatal diagnosis of single gene disorders by analysis of fetal cells in maternal blood: Successful application in sickle cell anemia and β–thalassemia," *Abstracts of the American Journal of Human Genetics*, 4(59) Suppl.) :All #46 (1996).
de la Cruz, et al., "Prenatal diagnosis by use of fetal cells isolated from maternal blood," *Am. J. Obstet. Gynecol.*, 173(4): 1354–1355 (1955).
Emery and Rimoin (as edited), "Haemoglobinopathies and thalassaemias," *Principles and Practice of Medical Genetics*, J.A. Phillips and H.H. Kazazian, 1023–1024 (1983).
Iwahara, et al., "Identification of Five Embryonic Hemoglobins of Rat and Ontogeny of Their Constituent Globins During Fetal Development," *J. Biochem*, 119(2): 360–366 (1966).
Kleihauer, et al., "Demonstration von Fetalem Hämoglobin in Den Erythrocyten Eines Blutasstrichs", *Klin. Wschr.* 35:637–638 (1957).
Kutlar, et al., "Quantities of Adult, Fetal and Embryonic Globin Chains in the Blood of Eighteen–to Twenty–Week–Old Human Fetuses." *Journal of Chromatography*, 567:2 (Jul. 5, 1991), 359–368. Abstract Only.
Lo, et al., "Prenatal Sex Determination by DNA Amplification from Maternal Peripheral Blood," *Lancet*, 2:1363–1365 (1989).
Martens, et al., "A New Method of Detection and Confirmation of Fetal Nucleated Red Blood Cells from Maternal Blood," *Abstracts of the American Journal of Obstetrics and Gynecology*, 170 (1 Pt. 2):282 #43 (1994).

(List continued on next page.)

Primary Examiner—Jeffrey Stucker
Attorney, Agent, or Firm—Townsend & Townsend & Crew LLP

[57] ABSTRACT

An in vitro method of identifying or isolating fetal cells from a blood sample is described. Fetal nucleated erythrocytes or erythroblasts are identified by using an antibody or antibody fragment specific for embryonic hemoglobin or an embryonic hemoglobin chain. Once the fetal cells are identified, they can be treated to render the fetal nucleic acids or proteins available for identification or amplification. Detecting the occurrence or existence of selected fetal nucleic acids or proteins allows a quantitative or qualitative diagnostic or prenatal evaluation, including determining the sex of the fetus, determining chromosomal, single gene or protein abnormalities, and determining the presence or absence of particular genes, nucleic acid sequences or proteins.

14 Claims, No Drawings

OTHER PUBLICATIONS

O'Kelly, et al., "Instrumentation for the genetic evaluation of fetal cells from maternal blood," *Abstracts of the Amer. Coc. Hum. Genet.,* A286 #1661 (1995).

Oosterwijk, et al., "Detection of fetal erythroblasts in maternal blood by one–step enrichment, immunocytochemical recognition, Fish analysis and automated microscopy," *Abstracts of the American Journal of Human Genetics,* 4(59) Suppl.):A327 #1903 (1996).

Park, et al., "A Model System Using Fetal Hemoglobin to Distinguish Fetal Cells Enriched from Maternal Blood," *Ann. NY Acad. Sci.,* 731:133–135 (1994).

Saunders, et al., "Enrichment of Fetal Cells from Maternal Blood for Genetic Analysis", *Abstracts of the Amer. Soc. Hum. Genet.,* Abstract No. A287 1672 (1995).

Simpson, et al., "Isolating fetal cells in maternal circulation," *Human Reproduction Update,* 1(4):409–418 (1995).

Simpson, et al., "Fetal Cells in Maternal Blood, Overview and Historical Perspective," *Ann. NY Acad. Sci.,* 731:1–8 (1994).

Simpson, et al., "Isolating Fetal Cells in Maternal Circulation for Prenatal Diagnosis," *Prenat. Diagn.,* 14:1229–1242 (1994).

Simpson, et al., "Isolating Fetal Nucleated Red Blood Cells from Maternal Blood: the Baylor Experience—1995," *Prenat. Diagn.,* 15:907–912 (1995).

Simpson, et al., "Noninvasive Screening for Prenatal Genetic Diagnosis," *Bull. Who,* 73(6):799–804 (1995).

Strickberger, *Genetics (3d Ed.),* MacMillan, New York, 541 (1985).

Weber, et al., "HbA and HbF mRNA Expression in Fetal Nucleated Erythrocytes from Cord Blood," *Abstracts of the American Journal of Human Genetics,* 57(4 Suppl.):A291 #1691 (1995).

Weber, et al., "Embryonic pig hemoglobins Gower I (zeta 2 epsilon 2), Gower II (alpha 2 epilson 2), Heide I (zeta 2 theta 2) and Heide II (alpha 2 theta 2): oxygen binding functions related to structure and embryonic oxygen supply," *Respir. Physiol.,* 69:347–357 (1987).

Zheng, et al., "Flow Sorting of Fetal Erythroblasts Using Intracytoplasmic Anti–Fetal Haemoglobin: Preliminary Observations on Maternal Samples," *Prenat. Diagn.,* 15:897–905 (1995).

USE OF ANTI-EMBRYONIC EPSILON HEMOGLOBIN ANTIBODIES TO IDENTIFY FETAL CELLS

CROSS-REFERENCE TO RELATED APPLICATIONS

This application is the national phase counterpart of International Application PCT/US97/19447, filed on Oct. 20, 1997, which claims priority to U.S. application Ser. No. 08/734,556, filed on Oct. 21, 1996, now U.S. Pat. No. 5,731,156, issued on Mar. 24, 1998.

This invention relates to a method for separating and recognizing fetal cells from a blood sample. More particularly, it relates to the isolation and recognition of fetal nucleated erythrocytes or erythroblasts from maternal cells in a blood sample from a pregnant woman.

BACKGROUND OF THE INVENTION

Fetal tissue, and in particular fetal DNA and chromosomes, is routinely used in prenatal diagnosis and other medical procedures that require an accurate assessment of the genome of the fetus. Currently, the fetal tissue is obtained by the use of amniocentesis, chorionic villus sampling (CVS), fetoscopy, or cordocentesis, as described in Thompson and Thompson Genetics in Medicine, 5th Edition, W. B. Saunders Co., Philadelphia, 1991.

In amniocentesis, a sample of amniotic fluid, which contains fetal cells, is transabdominally removed from the mother with a needle and syringe. Amniocentesis has inherent associated risks. The major risk is induction of miscarriage which is estimated to occur in 1 in 200 amniocenteses. Other risks include maternal infection and physical damage to the fetus. In CVS, trophoblast tissue is aspirated from the villous area of the chorion transcervically or transabdominally. The rate of fetal loss by this method may be as high as 1 in 100. Cordocentesis or percutaneous umbilical blood sampling provides a method of obtaining fetal blood directly from the umbilical cord with ultrasonic guidance. Each of these invasive methods carries risks to both the mother and the fetus.

Accordingly, it would be desirable to have a noninvasive method for obtaining fetal tissue or fetal DNA. It would also be desirable to have a method that is rapid and reliable for isolating and enriching the fetal tissue from maternal tissue in order to facilitate screening and pre-natal diagnosis in clinical laboratories. Recently, the preferred methodology has been the identification of fetal cells in the peripheral maternal circulation and then garnering of those cells for genetic analysis.

Identification or isolation of fetal cells from maternal blood has relied upon distinguishing the rare population of fetal cells from the more prevalent maternal cells. Although various fetal cell types, such as fetal lymphocytes and trophoblasts, have been utilized in the identification process as target cells for fetal DNA, more efforts have been directed to fetal nucleated red blood cells (nRBC), also known as nucleated erythrocytes. See Cheuh and Golbus, "The Search for Fetal Cells in the Maternal Circulation", *J. Perinatol. Med.*, 19:411 (1991); Simpson, et al., "Noninvasive Screening for Prenatal Genetic Diagnosis", Bull. WHO, 73:799 (1995); and Cheuh and Golbus, "Prenatal Diagnosis Using Fetal Cells from Maternal Circulation", *West. J. Med.*, 159(3):308 (1993).

Fetal RBCs are thought to cross the placenta as a result of transplacental bleeding. Since the fetus has a large number of nucleated erythrocytes, which nucleated erythrocytes are rarely found in adult blood, the difference in nucleation is useful in separating and identifying fetal cells from maternal ones.

Antibodies to cell surface antigens particular to nRBCs, such as the transferrin receptor, have been utilized to identify and enrich for these fetal cells. See Bianchi, et al., "Isolation of Fetal DNA from Nucleated Erythrocytes in Maternal Blood", *Proc. Natl. Acad. Sci*, 87:3279 (1990). See also Bianchi, et al. PCT International Application No. PCT/US90/06623 (WO 91/07660), which describes a method for enriching fetal nucleated red blood cells from a peripheral blood sample by the use of an antibody which binds an antigen on the cell surface of the fetal cells.

Bresser, et al., PCT International Application No. PCT/US94/08342 (WO 95/03431) describes the use of fetal hemoglobin antibodies and mRNA probes to enrich for fetal cells in maternal blood. The presence of fetal hemoglobin also has been demonstrated by the Kleihauer-Betke reaction that differentiates fetal from adult hemoglobin by acid elution characteristics. See Kleihauer, et al., "Demonstration von fetalem hamoglobin in den erythrocyten eines blutausstrichs", *Klin. Woschenschr*, 35:637 (1957); and Saunders, et al., "Enrichment of fetal cells from maternal blood for genetic analysis", *American Journal of Human Genetics*, 57:287 (1995).

Genetic analysis of the fetal genome has been accomplished by fluorescence in situ hybridization (FISH) of chromosome or gene specific DNA or RNA probes, sometimes with automated reading, and by amplification of targeted fetal genes or DNA. See Lichter, et al., "Rapid detection of human chromosome 21 aberration analysis using fluorescence in situ hybridization", Proc. Natl. Acad. Sci., 85:9664 (1988); O'Kelley, et al., "Instrumentation for the genetic evaluation of fetal cells from maternal blood", *Am. J. Hum. Genet.*, 57:286 (1995); and Lo, et al., "Prenatal Sex Determination by DNA amplification from maternal peripheral blood", Lancet, 2:1363 (1989).

SUMMARY OF THE INVENTION

The present invention provides a method of identifying a fetal erythrocyte, preferably nucleated, or an erythroblast cell in a blood sample, the method comprising a) contacting the blood sample with an antibody, or antibody fragment thereof, directed to an embryonic globin portion of hemoglobin, wherein the antibody or fragment will bind the fetal cell; and b) identifying the cells which bind to the antibody or fragment as fetal nucleated erythrocyte or erythroblast cells.

(The blood sample is typically taken from the peripheral circulating maternal blood during gestation.)

Various anti-embryonic hemoglobin antibodies or antibody fragments thereof can be used in the method, preferably those directed to the embryonic epsilon globin chain and/or embryonic zeta globin chain of hemoglobin. In addition, second fetal or mature cell markers can be utilized to further identify or isolated the desired fetal cell.

Once the selected fetal cells are identified, a fetal nucleic acid or protein can be amplified or detected within the cell for genetic analysis.

Also provided by the invention are various kits for use in conjunction with the methods described above. These kits comprise a directly or indirectly labeled anti-embryonic hemoglobin antibody and instructions for use. Also optionally included within such kits are density gradient mediums for enriching the concentration of the fetal cells, hemolysis reagents for disrupting red blood cells, lysis agents, and nucleic acid probes.

DETAILED DESCRIPTION OF SPECIFIC EMBODIMENTS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, "erythrocytes" or "red blood cells" or "RBC" include adult and fetal red blood cells, and may be nucleated or non-nucleated. Nucleated erythrocytes are preferred.

As used herein, "erythroblast" means a nucleated precursor cell from which a reticulocyte develops into an erythrocyte. "Normoblast" means a nucleated red blood cell, the immediate precursor of an erythrocyte.

As used herein, "embryo" means a cell or cells from conception through the second month of gestation. Typically the developmental stages after the embryonic stage until birth are designated as fetal.

Fetal blood cells are rare cells circulating in the maternal blood stream. Fetal cells are believed to "leak" into the maternal blood stream through the placenta. Estimates of the frequency of this rare event vary, but have been reported as approximately 1 in $10^8$ to 1 in $10^{11}$ cells. Holzgreve, W. et al., *Lancet* (1990) i:1220. During the early period of gestation, fetal red blood cells may be nucleated. Thus, unlike non-nucleated fetal erythrocytes, they contain fetal DNA and can be used for genetic analysis of the fetus without the necessity of invasive procedures.

Ontogeny of Hemoglobin

Approximately 99% of adult hemoglobin is composed of two alpha chains and two beta chains with about 1% comprising two alpha chains and two delta chains. Fetal hemoglobin contains two alpha and two gamma chains.

Three earlier embryonic hemoglobins are constructed with zeta (alpha-like) and epsilon (beta-like chains). Embryonic Gower 2 is made up to two alpha chains and two epsilon chains, while embryonic Gower 1 hemoglobin is made up of two zeta chains and two epsilon chains, and embryonic hemoglobin Portland consists of two zeta chains and two gamma chains. See Gale, et al., *Nature*, 280:162 (1979); and Maniatis, et al, *Ann. Rev. Genetics*, 14:145 (1980).

Through the present invention it has been demonstrated that embryonic globin chains are still present in fetal RBCs up to about 22 menstrual weeks of gestation, although the messenger RNA is no longer present. Preferably, these chains are detected from about 9 to about 20 menstrual weeks. The fetus eventually switches to the production of fetal hemoglobin, which is found as approximately 1% of the hemoglobin in an adult. There are no embryonic hemoglobins in the adult RBCs.

Hemoglobin Antibodies

The various specific hemoglobins in RBCs can be distinguished using antibodies or antibody fragments specific to the antigenic sites of the globin chain. Antibodies to adult globins (alpha and beta), to fetal globin (gamma) and to embryonic epsilon globin are commercially available. Accurate Chemical and Scientific Corporation (Westbury, N.Y.), and Cortex Biochem (San Leandro, Calif.) supply the epsilon globin antibody.

A number of immunogens can be used to produce antibodies specifically reactive with hemoglobin chain proteins. Recombinant protein is the preferred immunogen for the production of monoclonal or polyclonal antibodies. Naturally occurring protein also can be used either in pure or impure form. Synthetic peptides made using the hemoglobin chain protein amino acid sequence also can be used as an immunogen for the production of antibodies to the proteins. Recombinant protein can be expressed in eukaryotic or prokaryotic cells, and purified. The product is then injected into an animal capable of producing antibodies.

Methods of production of polyclonal antibodies are known to those of skill in the art. In brief, an immunogen, preferably a purified protein, is mixed with an adjuvant and animals are immunized. The animal's immune response to the immunogen preparation is monitored by taking test bleeds and determining the titer of the reactivity. When appropriately high titers of antibody to the immunogen are obtained, blood is collected from the animal and antisera are prepared. Further fractionation of the antisera to enrich for antibodies reactive to the protein can be done if desired. See Harlow, et al, *Antibodies. A Laboratory Manual*, Cold Spring Harbor Publications, New York (1988).

Monoclonal antibodies can be obtained by various techniques familiar to those skilled in the art. Briefly, spleen cells from an animal immunized with a desired antigen are immortalized, commonly by fusion with a myeloma cell. See Kohler, et al., *Eur. J. Immunol.*, 6:511–519 (1976). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells can be enhanced by various techniques, including injection into the peritoneal cavity of the vertebrate host. Alternatively, one can isolate DNA sequences which encode a monoclonal antibody or a binding fragment thereof by screening a DNA library from human B cells according to the general protocol outlined by Huse, et al., *Science*, 246:1275–1281 (1989).

Various components or fragments of antibodies can be used in the present invention. The variable regions of an immunoglobulin are the portions that provide antigen recognition specificity. In particular, the specificity resides in the complementary determining regions (CDRs), also known as hypervariable regions, of the immunoglobulins. The immunoglobulins may exist in a variety of forms including, for example, Fv, Fab, F(ab'), F(ab')$_2$, and other fragments, as well as single chains. See Huston, et al., *Proc. Nat. Acad. Sci. U.S.A.*, 85:5879–5883 (1988) and Bird, et al., *Science* 242:423–426 (1988). See, generally, Hood, et al., *Immunology*, Benjamin, N.Y., 2nd ed. (1984), and Hunkapiller and Hood, *Nature*, 323:15–16 (1986). Single-chain antibodies, in which genes for a heavy chain and a light chain are combined into a single coding sequence, can also be used. Immunoglobulin polypeptide also encompasses a truncated immunoglobulin chain, for example, a chain containing less constant region domains than in the native polypeptide. Such truncated polypeptides can be produced by standard methods such as introducing a stop codon into the gene sequence 5' of the domain sequences to be deleted. The truncated polypeptides can then be assembled into truncated antibodies. Antibodies as used herein also include bispecific antibodies which can be produced such as by the methods described in the following references: Glennie et al., *J. Immunol.*, 139:2367–2375 (1987); Segal, et al., *Biologic Therapy of Cancer Therapy of Cancer Updates*, 2(4):1–12 (1992); and Shalaby, et al., *J. Exp. Med.*, 175:217–225 (1992). Monospecific and bispecific immunoglobulins can also be produced by recombinant techniques in prokaryotic or eukaryotic host cells.

"Chimeric" antibodies are encoded by immunoglobulin genes that have been genetically engineered so that the light and heavy chain genes are composed of immunoglobulin gene segments belonging to different species. For example, the variable (V) segments of the genes from a mouse monoclonal antibody may be joined to human constant (C) segments. Such a chimeric antibody is likely to be less antigenic to a human than antibodies with mouse constant regions as well as mouse variable regions.

As used herein, the term chimeric antibody also refers to an antibody that includes an immunoglobulin that has a human-like framework and in which any constant region present has at least about 85–90%, and preferably about 95% polypeptide sequence identity to a human immunoglobulin constant region, a so-called "humanized" immunoglobulin. See for example, PCT Publication WO 90/07861. Hence, all parts of such a "humanized" immunoglobulin, except possibly the complementary determining regions (CDRs), are substantially identical to corresponding parts of one or more native human immunoglobulin sequences. Where necessary, framework residues also can be replaced with those within or across species especially if certain framework residues are found to affect the structure of the CDRs. A chimeric antibody can also contain truncated variable or constant regions.

The term "framework region", as used herein, refers to those portions of immunoglobulin light and heavy chain variable regions that are relatively conserved (i.e., other than the CDRs) among different immunoglobulins in a single species, as defined by Kabat, et al., *Sequences of Proteins of Immunologic Interest*, 4th Ed., U.S. Dept. Health and Human Services (1987). As used herein, a "human-like framework region" is a framework region that in each existing chain comprises at least about 70 or more amino acid residues, typically 75 to 85 or more residues, identical to those in a human immunoglobulin.

Human constant region DNA sequences can be isolated in accordance with well known procedures from a variety of human cells, but preferably from immortalized B-cells. The variable regions or CDRs for producing the chimeric immunoglobulins of the present invention can be similarly derived from monoclonal antibodies capable of binding to the embryonic hemoglobins or their chains and will be produced in any convenient mammalian system, including, mice, rats, rabbits, human cell lines, or other vertebrates capable of producing antibodies by well known methods. Variable regions or CDRs may be produced synthetically, by standard recombinant methods including polymerase chain reaction (PCR) or through phage-display libraries. For phage display methods, see for example, McCafferty, et al., *Nature*, 348:552–554 (1990); Clackson, et al., *Nature*, 352:624–628; and Marks, et al., *Biotechnology*, 11:1145–1149 (1993). Suitable prokaryotic systems such as bacteria, yeast and phage can be employed.

Suitable source cells for the DNA sequences and host cells for immunoglobulin expression and secretion can be obtained from a number of sources, such as the American Type Culture Collection ("Catalogue of Cell Lines and Hybridomas," Fifth edition (1985) Rockville, Md., U.S.A.).

In addition to the chimeric and "humanized" immunoglobulins specifically described herein, other substantially identical modified immunoglobulins can be readily designed and manufactured utilizing various recombinant DNA techniques well known to those skilled in the art. In general, modifications of the genes can be readily accomplished by a variety of well-known techniques, such as PCR and site-directed mutagenesis. See Gillman and Smith, *Gene*, 8:81–97 (1979) and Roberts, et al., *Nature*, 328:731–734 (1987).

Alternatively, polypeptide fragments comprising only a portion of the primary immunoglobulin structure can be produced. For example, it may be desirable to produce immunoglobulin polypeptide fragments that possess one or more immunoglobulin activities in addition to, or other than, antigen recognition (e.g., complement fixation).

Labels

The antibodies or fragments can be labeled directly or indirectly for their isolation and identification. Suitable labels include radionuclides, enzymes, substrates, cofactors, inhibitors, fluorescers, chemiluminescers, magnetic articles, haptens, dyes, and the like. See U.S. Pat. Nos. 3,817,837; 3,850,752; 3,939,350; 3,996,345; 4,277,437; 4,275,149; and 4,366,241. Also included are reporter groups, such as biotin, which bind to groups such as streptavidin or avidin, which in turn are bound directly or indirectly to enzymes, such as alkaline phosphatase or horseradish peroxidase. Fluorescers or fluorochromes include fluorescein, coumarin, rhodamine, phycoerythrin, sulforhodamine acid chloride (Texas red), and the like.

These detectable labels have been well-developed in the field of the invention and, in general, most any label can be applied. Preferably, enzymes or fluorescers are utilized.

Blood Sampling

The method of the present invention preferably utilizes a blood sample from the mother during gestation; however, other sources of fetal cells can be used besides those isolated or identified in the maternal circulation. Fetal tissue can be obtained via amniocentesis, CVS, fetoscopy or cordocentesis for analysis as described above.

In those instances wherein maternal blood is the source of fetal cells, the blood sample can be whole blood or a fractionated component of the blood containing the fetal erythrocyte or erythroblast cells of choice in a mononuclear cell layer. Typically, the blood source is prepared to enrich the concentration of fetal cells before and/or after the use of the anti-embryonic hemoglobin antibody of the claimed method. Further, the blood sample can be suspended, air-dried, or chemically-fixed on to a solid matrix before contact with the antibody.

Although any maternal or fetal mammal can be the source of fetal tissue, the preferred source is human. Other domestic mammals are also preferred, such as dogs, cats, cows horses and the like.

Enrichment Methods Density Gradients

In addition to blood fractionation, methods for the isolation or enrichment of blood cells have been described which use density gradients containing cell aggregating or clumping agents such as methylcellulose, Isopaque™, dextran and Ficoll™, as described in Boyum, *Scand. J. Clin. Lab. Invest.*, 21 (*Suppl.*97):31–50 (1968), and in Bhat, *N. M. J. Immunol. Meth*, 158:277–280 (1993). Isopaque™ is a sodium N-methyl-3,5,-diacetamino-2,4,6-triiodobenzoate, as described in Boyum. Ficoll™ (Accurate Chemical and Scientific Corporation, Westbury N.Y.) is a synthetic high polymer made by the copolymerization of sucrose and epichlorohydrin. The molecules have a branched structure with a high content of hydroxyl groups giving solubility in aqueous media. Many of these agents are freely diffusible. These agents cause erythrocyte clumping, and thus provide methods for isolating leukocytes from red blood cells. However, under these cell-aggregating conditions, fetal nucleated red blood cells may become physically trapped within a clump of aggregated maternal red blood cells, and therefore will sediment with maternal erythrocytes, as the average density of the clump determines its sedimentation characteristics.

Percoll density gradients have been described in Rennie, et al *Clinica Chemica Acta,* 98:119–125 (1979), and in Vincent and Nadeau, *Anal. Biochem.,* 141:322–328 (1984). In the Rennie study, an isotonic Percoll density gradient was used to age-fractionate erythrocytes. Leukocytes (white blood cells) were removed prior to the centrifugation process, as they co-fractionated with erythrocytes in isotonic gradient conditions.

Ganshert-Ahlert, et al, *Am. J. Obstet. Gynecol.,* 1350–1355 (1992) and PCT Publication WO 93/23754, describe a method of enriching for fetal nucleated erythrocytes using a triple density gradient on whole maternal blood, followed by use of the transferrin receptor to enrich fetal nucleated red blood cells. A flow cytometry or magnetic separation step is required to enrich the labelled cells. As noted in the Ganshert-Ahlert reference, the use of the transferrin receptor still does not provide a reliable identification of fetal cells in a circulating maternal cell population.

A preferred enrichment method for isolating fetal nucleated red blood cells from a maternal population comprises the steps of centrifuging the blood sample in a first centrifugation vessel to obtain a red blood cell fraction; transferring the red blood cell fraction to an upper portion of a second centrifugation vessel, the second centrifugation vessel having a density gradient medium consisting of a colloid dispersed in a meltable gel, wherein the colloid is capable of maintaining the red blood cells in a substantially unaggregated state; hemolyzing maternal erythrocytes in the red blood cell fraction to obtain an enriched fetal erythrocyte fraction; melting the gel; and centrifuging the enriched fetal erythrocyte fraction through the density gradient medium to obtain a fraction enriched in fetal nucleated erythrocytes. See U.S. Pat. No. 5,432,054.

The first centrifuge step provides an initial enrichment which separates the low density nucleated red blood cell fraction and all the white blood cells from the more dense un-nucleated red blood cells, and from the serum, and serum proteins. Preferably, the first centrifuge tube is made of soft plastic, in order to facilitate the movement of the blood cells through the tube. Suitable tubes are described in U.S. Pat. No. 5,422,018. Plastic hourglass shaped tubes are preferably supported within the centrifuge, to prevent excessive deformity or collapse of the tube at the narrow central channel portions. Support may be provided by any suitable means. For example, a solid removable support cast may be wrapped around the tube. In a preferred embodiment, the tube is supported in a liquid support medium within a larger vessel, such as a test tube. The level of liquid is at least high enough to cover the narrow portion of the tube. Preferably, the weight of the volume of the liquid support medium displaced by the sample tube is approximately equivalent to the weight of the volume of the sample tube and its contents. A preferred liquid support medium for use is water.

After the first centrifugation step, a fraction containing the nucleated red blood cells is obtained. This fraction also includes the white blood cells. The top of the tube contains the plasma fraction. The nucleated red blood cells, which are more dense than plasma but less dense than other red blood cells, will fractionate at the top of the red blood cell stack found just below the plasma and will be variably mixed with white blood cells. The use of a precalibrated first centrifuge tube permits easy extraction of the relevant fraction from the narrow portion of the first tube, thus minimizing inclusion of other blood fractions, including serum and plasma from the first centrifugation step.

The fraction containing the red blood cells and white blood cells can be hemolyzed to differentially disrupt the maternal red blood cells. Differential hemolysis of the maternal red blood cells permits the destruction of a significant number of the remaining maternal red blood cells while preserving the majority of the fetal-origin cells. See Boyer, et al, *Blood,* 47(6):883–897 (1976). The differential hemolysis may occur in any suitable reaction vessel. In a preferred embodiment, the differential hemolysis of the maternal red blood cells occurs in an upper portion of the second centrifugation vessel, such that the hemolysis reaction may be stopped by centrifuging the reaction products, i.e. the preserved red blood cells, into the density gradient medium, thus removing the red blood cells from the hemolysis reagents.

The differential hemolysis utilizes the fact that red blood cells may be disrupted in solutions containing hemolyzing agents such as ammonium ($NH_4$—) and bicarbonate ($HCO_3$—) ions. The cell disruption may be decelerated by inhibitors of the enzyme carbonic anhydrase. Carbonic anhydrase levels are at least five fold higher in adult erythrocytes than in fetal erythrocytes. Thus, the rate of $NH_4$— $HCO_3$ mediated hemolysis is slower for fetal red blood cells, including fetal nucleated red blood cells, than for adult red blood cells, particularly in the presence of carbonic anhydrase inhibitors. Preferred carbonic anhydrase inhibitors for use in the invention include acetazolamide, ethoxzolamide (6-ethoxyzolamide, Sigma Chemical Co.) and methoxzolamide.

Differential hemolysis results in a population of white blood cells together with red blood cells enriched for fetal red blood cells. The enriched fetal red blood cell fraction is then centrifuged through the density gradient medium in order to harvest the fraction enriched for fetal nucleated red blood cells, and to remove red blood cell fragments resulting from the hemolysis reaction and the majority of white blood cells. The fetal nucleated red blood cells present in an initial sample of 20 ml of peripheral blood may be reduced into a 2 microliter sample, thus providing easy identification and analysis on a microscope slide, or by polymerase chain reaction.

The second centrifugation step utilizes a density gradient medium. After hemolysis, the nucleated red blood cells are expected to equilibrate in a density gradient at approximately the same density as granulocytes, a component of the white blood cell fraction, as described in PCT International Application No. WO 93/23754. The tonicity and density of the gradient medium can allow separation and enrichment of the fetal nucleated erythrocytes from the white blood cell components of the sample.

The preferred density gradient medium is comprised of a colloid dispersed in a meltable gel. See U.S. Pat. No. 5,489,386. The colloid imparts the required density to the gradient medium. Thus, by altering the concentration of the colloid, the density of the medium may be correspondingly altered. The particulate nature of the colloid enables immobilization of separate layers of density without diffusion of one layer into another while in the gel state. Further, the colloid is capable of maintaining the blood cells in a substantially unaggregated state. A preferred colloid which imparts the density to the medium is polyvinyl-pyrrolidone coated silica, for example, Percoll™, manufactured by Pharmacia, and available from Sigma Chemical Co.

The density gradient medium for use in enriching fetal nucleated erythrocytes is hypertonic. Under hypertonic conditions, red blood cells shrink and thus become more dense. Under these conditions, white blood cells maintain a constant density. Thus, by selectively shrinking the erythrocytes in a hypertonic medium, the density of these cells increases and they equilibrate within the gradient at a different density from the white blood cells.

Enrichment Methods—Flow Cytometry and Others

Enrichment of the blood sample can be accomplished using other techniques, such as cell panning, microdissection using light microscopy, flow cytometry, and/or magnetic bead or particle separation. For example, antibodies specific to maternal or mature cell markers, and/or antibodies specific to a second fetal marker can be added to the method of the present invention to further enrich the sample for fetal cells. Either a positive or negative selection approach can be applied, i.e., enhancing the desired fetal cells or eliminating the unwanted mature cells. The use of an antibody-bound column can be used alone or in conjunction with other enrichment techniques.

Mueller, et al, in *Lancet,* 336:197 (1990) described a method of isolating placenta-derived trophoblast cells in the blood of pregnant women using magnetic beads. Other variations in methods for conjugating antibodies to beads also exist. See Thomas, et al., *J. Immunol.,* 120:221 (1989) and deKretser, et al., *Tissue Antigens,* 16:317 (1980). An alternative method of enrichment was discussed in Berenson, et al., *J. Immunol. Methods,* 91:11 (1986) in which the high affinity between the protein avidin and the vitamin biotin was exploited to create an indirect immunoadsorptive procedure.

In flow cytometry, cells can be analyzed and sorted on a flow sorter based on the properties of the cells to scatter light forward and to the side. In each experiment parameters are empirically established regarding the forward and side scatter properties. In general, the gain on the photomultiplier tubes detecting the forward-scatter light and the side-scattered light is adjusted in each dimension to distribute the array of signals from the cells across the channels available for analysis in a manner well known to one skilled in the art. Under these circumstances a characteristic pattern, or scattergram, is observed. Analysis of blood samples reveals three major cell types in the scattergram, namely, monocytic cells, lymphocytes and granulocytes, each of which has distinguishable light scattering characteristics. The monocytic cell region, the granulocytic cell region and the lymphocytic cell region of the scattergram are gated so that cells which are classified as monocytes, granulocytes or lymphocytes can be analyzed further or collected by flow sorting.

Further analysis can be carried out by staining the cells with florescent-coupled monoclonal antibodies or by subjecting the cells to in situ hybridization with fluorescent-coupled oligonucleotide or nucleic acid probes. Under these conditions cells that have particular light scattering properties are also analyzed for the presence of fluorescence. When fluorescent-coupled antibodies are used, control experiments are performed using isotypically matched control monoclonal antibodies. When fluorescent-coupled oligonucleotide probes are used, controls consist of oligonucleotide sequences unrelated to mammalian sequences.

Collected samples are deposited on one or more slides, with no more than 2–3,000,000 cells deposited on any single slide; care is taken that deposited cells form a monolayer such that the concentration of cells on the slide is low enough so that the cells do not overlap one another. At other times, the cells are collected into microfuge tubes and fixed in suspension as described elsewhere.

A Coulter, Profile II, flow cytometer (Coulter, Haileah, Fla.) can be used to detect nucleic acids within fetal cells. An Epics Elite, (Coulter, Haileah, Fla.) system can be used to sort fetal cells from a specimen of maternal blood.

Preferably, a fluorescence activated cell sorter (FACS) is used to perform flow cytometry and to identify the fetal cells, using fluorescein as the label or dye directly or indirectly bound to the antibody.

Other Markers

A second fetal marker can be used to define the cell as fetal. For example, antibodies to representative fetal cell markers can be used. For fetal red blood cells, a fetal hemoglobin marker, such as an antibody to the fetal gamma chain of hemoglobin, is preferable.

Fetal-cell-specific RNA sequences also can be used as fetal cell markers. Such sequences are transcripts of, e.g., the fetal hemoglobin gene. The sequences of these genes and others may be obtained from the Genetic Sequence Data Bank, GenBank, version 69.0. A DNA probe, or population of probes, embodying any of these sequences is synthesized as an oligodeoxynucleotide using a commercial DNA synthesizer such as Model 380B from Applied Biosystems, Inc., Foster City, Calif. Probes can be comprised of the natural nucleotide bases or know analogues of the natural nucleotide bases, including those modified to bind labeling moieties.

For negative selection, a mature cell marker can be used, such as an antibody to anti-CD45, anti-CD13 and/or anti-CD34, which selectively binds to white blood cells. Anti-CD44 antibodies can be included to remove contaminating maternal red blood cells. The addition of anti-CD31 antibodies can specifically remove contaminating platelets. Preferably, antibodies directed to the adult beta chain of hemoglobin can be utilized.

Fetal Nucleic Acids and Proteins

Once the fetal cells are isolated from the maternal blood, they can be cultured to increase the numbers of cells available for diagnosis. See Fibach, et al., *Blood,* 73:100 (1989).

Particular fetal proteins and/or nucleic acids can be selected or isolated as follows. The cells can be lysed and thereby rendering the nucleic acid or protein available for analysis. In some instances, fetal DNA can be extracted from other complexes, e.g., by heat, making it accessible for hybridization with nucleic acid probes. Prior to analysis, the fetal DNA can be amplified via methods such as polymerase chain reaction (PCR) or ligase chain reaction (LCR).

If amplification is to be carried out, the sorted samples are amplified for an appropriate number of cycles of denaturation and annealing (e.g., approximately 25–60). Control samples can include a tube without added DNA to monitor for false positive amplification. With proper modification of PCR conditions, more than one separate fetal gene can be amplified simultaneously. This technique, know as "multiplex" amplification, has been used with six sets of primers in the diagnosis of DMD. See Chamberlin, et al., *Prenat. Diagn.,* 9:349–355 (1989). When amplification is carried out, the resulting amplification product is a mixture that contains amplified fetal DNA of interest, i.e., the DNA whose occurrence is to be detected and/or quantitated.

The amplified fetal DNA of interest and other DNA sequences are separated, using known techniques. Subsequent analysis of amplified DNA also can be carried out using known techniques, such as: digestion with restriction endonuclease, ultraviolet light visualization of ethidium bromide stained agarose gels, DNA sequencing, or hybridization with allele specific oligonucleotide probes. See Saiki, et al., *Am. J. Hum. Genet.,* 43 (Suppl.):A35 (1988). Such analysis will determine whether polymorphic differences exist between the amplified "maternal" and "fetal" samples. The amplification mixture can be separated on the basis of size and the resulting size-separated fetal DNA is contacted with an appropriate selected DNA probe or probes (DNA sufficiently complementary to the fetal DNA of interest that it hybridizes to the fetal DNA of interest under the conditions used). Generally, the DNA probes are labelled using labels as described above.

After the size-separated fetal DNA and the selected DNA probes have been maintained for sufficient time under appropriate conditions for hybridization of complementary DNA sequences to occur, resulting in production of fetal DNA/DNA probe complexes, detection of the complexes is carried out using known methods. For example, if the probe is labelled, the fetal DNA/labelled DNA probe complex is detected and/or quantitated (e.g., by autoradiography, detection of the fluorescent label). The quantity of labelled complex (and, thus, of fetal DNA can be determined by comparison with a standard curve (i.e., a predetermined relationship between quantity of label detected and a given reading).

Detection of Genetic Abnormalities

The occurrence of fetal DNA associated with diseases or conditions can be detected and/or quantitated by the present method. In each case, an appropriate probe is used to detect the sequence of interest. For example, sequences from probes St14 (Oberle, et al, *New Engl. J. Med.,* 312:682–686 (1985)), 49a (Geurin, et al., *Nucleic Acids Res.,* 16:7759 (1988)), KM-19 (Gasparini, et al., *Prenat. Diagnosis,* 9:349–355 (1989)), or the deletion-prone exons for the Duchenne muscular dystrophy (DMD) gene (Chamberlain, et al., *Nucleic Acids Res.,* 16:11141–11156 (1988)) are used as probes. St14 is a highly polymorphic sequence isolated from the long arm of the X chromosome that has potential usefulness in distinguishing female DNA from maternal DNA. It maps near the gene for Factor VIII:C and, thus, can also be utilized for prenatal diagnosis of Hemophilia A. Primers corresponding to sequences flanking the six most commonly deleted exons in the DMD gene, which have been successfully used to diagnose DMD by PCR, can also be used. See Chamberlain, et al., *Nucleic Acids Res.,* 16:11141–11156 (1988). Other conditions which can be diagnosed by the present method include Down's Syndrome, β-thalassemia (Cai, et al., *Blood,* 73:372–374 (1989); Cai, et al., *Am. J. Hum. Genet.,* 45:112–114 (1989); Saiki, et al., *New Engl. J. Med.,* 319:537–541 (1988)), sickle cell anemia (Saiki, et al., *New. Engl. J. Med.,* 319:537–541 (1988)), phenylketonuria (DiLella, et al., *Lancet,* 1:497–499 (1988)) and Gaucher's disease (Theophilus, et al., *Am. J. Hum. Genet.,* 45:212–215 (1989)).

The genetic abnormalities detected by the present invention can be deletions, additions, amplifications, translocations or rearrangements.

For example, a deletion can be identified by detecting the absence of hybridizable binding of the probe to a target sequence. To detect a deletion of a genetic sequence, a population of probes are prepared that are complementary to the nucleic acid sequence that is present in a normal fetal cell but absent in an abnormal one. If the probes hybridize to the sequence in the cell being tested, then the sequence is detected and the cell is normal as to that sequence. If the probes fail to hybridize to cellular nucleic acid, then the sequence is not detected in that cell and the cell is designated as abnormal, provided that a control sequence, such as the X chromosome, is detected in the same cell.

An addition can be identified by detecting binding of a labeled probe to a polynucleotide repeat segment of a chromosome. To detect an addition of a genetic sequence, such as an insertion in a chromosome or a karyotypic abnormality such as the trisomy of Chromosome 21 which indicates Down's Syndrome, a population of probes are prepared that are complementary to the genetic sequence in question. Continuing with the Down's Syndrome example, if the probes complementary to Chromosome 21 hybridize to three appearances of the Chromosome 21 sequence in the cell, then three occurrences of the Chromosome 21 sequence will be detected and indicate the Down's Syndrome trisomic condition. If the detection means is a fluorescent dye, for example, then three distinct points of fluorescence visible in each cell will indicate the trisomy condition.

When an amplification of a particular DNA fragment is present, there is an increase in the intensity of the signal from a labeled probe for the sequence which is subject to amplification. Using any number of image analysis systems, this signal is quantified and compared to normal controls to determine whether or not a particular amplification mutation is present.

A translocation or rearrangement can be identified by several methods. For example, a labeled first probe may be bound to a marker region of a chromosome that has not translocated. A labeled second probe is then bound to a second region of the same chromosome (for a rearrangement) or a second chromosome (for a translocation) and subsequently binding of the first and second probes is detected. Alternatively, a translocation can be identified by first binding a labeled probe to a marker region of a polynucleotide section of a chromosome that translocates or rearranges, usually during metaphase. Subsequently, binding of the labeled probe is detected.

For example, to detect a translocation, a marker for the chromosome in question is identified, and a population of probes are prepared that selectively hybridize to it. They are marked with a detectable label, such as a dye that fluoresces at a particular wavelength. The sequence that translocates or rearranges in the abnormality being tested for is also identified, and second population of probes are prepared that identify it. The members of a second population of probes are marked with a distinguishably different label, such as a dye that fluoresces at a different wavelength from the first series of labeled probes. In situ hybridization is performed using both populations of probes, and the results of hybridization by each of the probe populations are compared. If the first and second labels are coincident on virtually all cell samples, no translocation has taken place. If the first label is found not to coincide with the second label on a significant fraction of samples, then a translocation or rearrangement has taken place. See Speleman, *Clinical Genetics,* 41(4):169–174 (1992); and Gray, *Progress in Clinical and Biol. Res.,* 372:399–411 (1991).

Nucleic Acid Hybridization

The term "nucleic acids", as used herein, refers to either DNA or RNA. "Nucleic acid sequence" or "polynucleotide sequence" refers to a single- or double-stranded polymer of deoxyribonucleotide or ribonucleotide bases read from the 5' to the 3' end. It includes both self-replicating plasmids, infectious polymers of DNA or RNA and nonfunctional DNA or RNA.

"Nucleic acid probes" may be DNA or RNA fragments. DNA fragments can be prepared, for example, by digesting plasmid DNA, or by use of PCR, or synthesized by either the phosphoramidite method described by Beaucage and Carruthers, *Tetrahedron Lett.*, 22:1859–1862 (1981), or by the triester method according to Matteucci, et al., *J. Am. Chem. Soc.*, 103:3185 (1981). A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid.

The phrase "selectively hybridizing to" refers to a nucleic acid probe that hybridizes, duplexes or binds only to a particular target DNA or RNA sequence when the target sequences are present in a preparation of total cellular DNA or RNA. "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook, et al., *Molecular Cloning: A Laboratory Manual*, (2nd ed.), Vols. 1–3, Cold Spring Harbor Laboratory, (1989) and Ausubel, et al., *Current Protocols in Molecular Biology*, ed. Greene Publishing and Wiley-Interscience, New York (1987).

Nucleic acids for use as probes are chemically synthesized according to the solid phase phosphoramidite triester method first described by Beaucage and Carruthers, *Tetrahedron Lett.*, 22(20):1859–1862 (1981) using an automated synthesizer, as described in Needham-VanDevanter, et al., *Nucleic Acids Res.*, 12:6159–6168 (1984). Purification of oligonucleotides is by either native acrylamide gel electrophoresis or by anion-exchange HPLC as described in Pearson and Regnier, *J. Chrom.*, 255:137–149 (1983). The sequence of the synthetic oligonucleotide can be verified using the chemical degradation method of Maxam and Gilbert, in Grossman and Moldave, eds. Academic Press, New York, *Methods in Enzymology*, 65:499–560 (1980).

A variety of methods for specific DNA and RNA measurement using nucleic acid hybridiziation techniques are known to those of skill in the art. For example, one method for evaluating the presence or absence of DNA in a sample involves a Southern transfer. Briefly, the digested genomic DNA is run on agarose slab gels in buffer and transferred to membranes. Hybridization is carried out using the nucleic acid probes. Preferably nucleic acid probes are 20 bases or longer in length. (See Sambrook, et al. for methods of selecting nucleic acid probe sequences for use in nucleic acid hybridization.) Visualization of the hybridized portions allows the qualitative determination of the presence or absence of DNA.

Similarly a Northern transfer may be used for the detection of mRNA. In brief, the mRNA is isolated from a given cell sample using an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify the presence or absence of appropriate mRNA.

A variety of nucleic acid hybridization formats are known to those skilled in the art. For example, common formats include sandwich assays and competition or displacement assays. Hybridization techniques are generally described in "Nucleic Acid Hybridiziation, A Practical Approach," Ed. Hames, and Higgins, IRL Press, 1985; Gall and Pardue, *Proc. Natl. Acad. Sci., USA*, 63:378–383 (1969); and John, Burnsteil and Jones, *Nature*, 223:582–587 (1969).

Ethanol, e.g., 80% ethanol/water (v/v), is desirably used as a fixative during preparation of the cells for in situ hybridization. Other useful precipitation fixatives include acetic acid, methanol, acetone, and combinations thereof, for example, ethanol/methanol mixture 3:1. Other useful fixatives will be known to one skilled in the art. Fixatives and hybridization of fixed cells, in general, are discussed in U.S. Pat. No. 5,225,326. Fixatives should provide good preservation of cellular morphology, should preserve and maintain accessibility of antigens, and promote a high hybridization efficiency. Some salts and extreme temperature, such as waving a slide over a flame, may also function as fixatives.

The fixative can contain a compound which fixes the cellular components by cross-linking these materials together, for example, paraformaldehyde, glutaraldehyde or formaldehyde. Cross-linking agents, while preserving ultrastructure, often reduce hybridization efficiency by forming networks trapping nucleic acids and antigens and rendering them inaccessible to probes and antibodies. Some cross-linking agents also covalently modify nucleic acids, preventing later hybrid formation.

The hybridization solution typically comprises a chaotropic denaturing agents include formamide, urea, thiocyantem guanidine, thrichloroacetate, tetramethyamine, perchlorate, and sodium iodide. Any buffer which maintains pH at least between about 6.0 and about 8.0 and preferably between 7.0 and 8.0 can be utilized.

Miscellaneous

Many types of solid supports can be used to practice the invention. Supports include glass, nylon, nitrocellulose and the like. Most preferably, glass or plastic microscope slides are use. The use of these supports and the procedures for depositing specimens thereon is known to those of skill in the art. The choice of support material will depend upon the procedure for visualization of cells and the quantitation procedure used.

In addition, nuclear stains can be used to recognize chromatin, nuclear proteins, nuclear components, DNA and the like. These stains include methylene blue, hematoxylin, DAP 1, propidinium iodide, thionin and the like.

Various chromosomal staining techniques also are encompassed by the present invention. Chromosomal painting is generally described in U.S. Pat. No. 5,447,841. Typically the heterogeneous mixtures of labelled nucleic acid fragments or probes are free from repetitive sequences. The entire genome, single chromosomes, subregions of chromosomes, and the like can be stained, usually during the metaphase cycle of the cell.

Kits

A kit for use in carrying out the present method of isolating and detecting fetal DNA of interest, such as a chromosomal abnormality associated with a disease or other condition, in a maternal blood sample can be produced. It includes, for example, a container for holding the reagents needed; the reagents and, optionally, a solid support for use in separating fetal nucleated cell/specific antibody complexes from other sample components or for removing maternal cells complexed with a specific antibody.

Preferably, provided by the invention is a kit for identifying a fetal nucleated erythrocyte or erythroblast cell comprising a labelled anti-embryonic hemoglobin antibody, wherein the label is a fluorochrome, enzyme, or biotin. Alternatively, the anti-embryonic hemoglobin antibody is conjugated with an antigenic hapten and a labeled second antibody directed to the hapten or hemoglobin antibody is used for capture. Other ingredients can be further components in the kit, such as a blood fractionation tube, hemolysis reagents, density gradient medium, lysis agents, labelled nucleic acid probes, and the like along with instructions for use.

For example, reagents in a kit to be used in detecting fetal DNA of interest after amplification of fetal DNA by PCR can include: 1) at least one antibody specific for an embryonic hemoglobin or chain; selected DNA primers for use in amplifying fetal DNA by PCR; and at least one DNA probe complementary to the fetal DNA to be detected (fetal DNA of interest). The kit, as indicated, can also include a solid support to be used in separating complexes formed from other samples components. Such solid support can be, for example, a glass slide, nitrocellulose filter, or immunomagnetic beads and can have affixes thereto an antibody selective for the antibody present in the fetal nucleated cell/specific antibody complexes. Other kits can include a solution containing a fixation/hybridization cocktail and one or more labeled probes. A kit also would provide means and instructions for performing the hybridization reaction. A kit could also include a photographic film or emulsion with which to record results of assays carried out with the invention.

Yet another aspect of the present invention would be a kit to enrich and detect fetal cells within a blood specimen, e.g., maternal or umbilical cord blood. Such a kit may contain one or more reagents to prepare a density gradient that concentrates fetal cells. Labeled antibodies to detect fetal cells and/or probes specific for fetal cell mRNA and/or DNA, and means and instructions for performing fetal cell enrichment also would be included.

An alternative kit can contain one or more antibodies, desirably bound to a solid support, to positively or negatively concentrate fetal cells within the specimen, probes specific for chromosome specific DNA sequences, means and instructions for performing fetal cell enrichment using density gradient centrifugation or flow cytometry, and optionally one or more reagents to prepare a density gradient that concentrates fetal cells.

Such a kit would optionally provide reagents and materials for use in an automated system for the performance of any of the methods of the present invention.

EXAMPLES

The following example is provided merely for the purposes of illustration and are not to be construed in any way as limiting the scope of the present invention. Those skilled in the art will recognize that certain variations and modifications can be practiced within the scope of the invention.

Wedge smears were prepared from 14-week gestation abortus cord blood, whole blood from the mother (post-abortion), and a 1:25 mixture of the above cord blood into the maternal blood sample. The smears were fan dried for about half hour at room temperature, fixed in 100% methanol at −20° C. for 10 minutes, and then in 100% acetone for 10 minutes at −20° C.

The slides were then washed in PBS (10 mM Phosphate Buffered Saline (pH 7.4) for 5 minutes at room temperature with moderate agitation and fixed in 2% formaldehyde/PBS at room temperature for 10 minutes with moderate agitation. After washing the slides twice in PBS for 5 minutes at room temperature with moderate agitation, the slides were washed twice in TBS (100 mM Tris-HCl pH 7.6) for 5 minutes at room temperature with moderate agitation.

The specimens were treated with blocking agent by depositing 200 $\mu$m of TNBB (0.5% blocking reagent (Boehringer Mannheim) and 1% BSA in 100 mM TBS) on a 24×60 coverslip for each side to be stained. The smears were then placed sample-side down onto the spot of TNBB. The slide-coverslip was placed coverslip-down in a plastic slide storage box, which in turn was placed in an open moist chamber containing water-dampened paper towels. Finally, the moist chamber was placed in a desiccator and a vacuum (Precision Vacuum Pump Model DD20) was applied to the entire construct for 15 minutes at room temperature. The slides were removed from the desiccator and immunostained.

The coverslips were gently removed and 100 $\mu$l of cocktail containing a 1:250 dilution of mouse anti-HbE (embryonic epsilon hemoglobin) (monoclonal) and a 1:10 dilution of rabbit anti-HbF (fetal gamma globin) (polyclonal) biotinylated antibody in TNBB/0.75% Tween 20 was added to each slide. The smear was covered with a fresh coverslip, and as above, the slide was incubated coverslip-down in a plastic slide storage box in a moist open chamber in a desiccator under vacuum for 15 minutes.

The coverslips were gently removed and the slides washed at room temperature with moderate agitation in TBS for 10 minutes, and then washed twice for 5 minutes. 100 $\mu$l of a second cocktail containing 1:100 dilution of FITC conjugated goat anti-mouse antibody and 1:100 dilution of Texas red conjugated horse anti-rabbit antibody in TNBB/0.75% Tween 20 was added to each slide and incubated under vacuum, as above.

The coverslips were gently removed and the slides washed at room temperature with moderate agitation in TBS for 10 minutes, and then washed twice for 5 minutes. The slides were then air dried and mounted in Vectrashield/DAPI.

Result:

The above system stained embryonic hemoglobin (hBE, epsilon hemoglobin) with green FITC fluorescence, and fetal hemoglobin (HbF, gamma hemoglobin) with Texas Red fluorescence. And addition, the nucleus of nucleated cells were stained blue by the DAPI counterstain.

The anti-HbE antibody (embryonic hemoglobin) was very specific. FITC fluorescence (embryonic hemoglobin) was observed only in red blood cells from the cord and cord-:maternal mixture smears. Both nucleated and mature HbE-positive red blood cells were observed. No FITC-stained white blood cells were found in any of the smears.

Texas Red fluorescence (gamma hemoglobin) was observed in mature red blood cells in all three smear types: cord, maternal, and mixture. It was also observed in nucleated red blood cells from the cord and cord:maternal mixture smears. Nucleated red blood cells, stained or otherwise, were not found in the maternal smear. Texas Red fluorescence is also observed in the cytoplasm of some granulocytes from cord and maternal smears. Whether this red fluorescence in granulocytes represented hemoglobin uptake by the granulocytes, or was an artifact of the polyclonal orgins of the antibody, is not known.

The cord and mixture smears also contained nucleated and mature red blood cells that stained positive for both gamma and embryonic hemoglobin.

All publications, patents, and patent applications herein are incorporated by reference to the same extent as if each individual publication or patent application was specifically and individually indicated to be incorporated by reference.

The foregoing description of the preferred embodiments of the present invention has been presented for purposes of illustration and description. They are not intended to be exhaustive or to limit the invention to the precise form disclosed, and many modifications and variations are possible in light of the above teaching, and are intended to be within the scope of the invention.

Although the foregoing invention has been described in some detail by way of illustration and example, for purposes of clarity of understanding, it will be obvious that certain changes and modifications may be practiced within the scope of the appended claims.

What is claimed is:

1. A method of identifying a fetal erythrocyte or erythroblast cell in a blood sample from a pregnant female from 9 to 22 menstrual weeks, the method comprising:
    a) contacting the blood sample with an antibody, or antibody fragment thereof, directed to an embryonic epsilon globin chain of hemoglobin, wherein the antibody or fragment is a first fetal marker and wherein the antibody or fragment will bind the fetal cell; and
    b) identifying the cells which bind to the antibody or fragment as fetal erythrocyte or erythroblast cells.

2. The method of claim 1 wherein the blood sample is human maternal blood and wherein the fetal erythrocyte is a nucleated erythrocyte.

3. The method of claim 1 wherein the antibody is a polyclonal antibody.

4. The method of claim 1 wherein the antibody is a monoclonal antibody.

5. The method of claim 1 wherein the antibody is directly or indirectly labelled.

6. The method of claim 1 further comprising contacting the blood sample with a second fetal marker.

7. The method of claim 6 wherein the second fetal marker is an antibody, or antibody fragment thereof, directed to the fetal gamma globin chain of hemoglobin.

8. The method of claim 1 further comprising contacting the blood sample with a mature cell marker.

9. The method of claim 8 wherein the mature cell marker is an antibody, or antibody fragment thereof, directed to the adult beta globin chain of hemoglobin.

10. The method of claim 1 further comprising enriching the concentration of the fetal cells in the blood sample before being contacted with the antibody or fragment, for the identification of the fetal cells.

11. The method of claim 10 wherein the fetal cells are enriched through flow cytometry, blood fractionation, density gradient separation, or magnetic bead separation.

12. The method of claim 1 further comprising selecting or isolating a nucleic acid or protein contained within the fetal cells after the fetal cells are identified.

13. The method of claim 12 wherein the nucleic acid or protein is amplified or detected.

14. The method of claim 1 wherein the fetal cells are collected, fixed, and placed in suspension.

* * * * *